United States Patent [19]

Hedengren

[11] Patent Number: 5,237,271

[45] Date of Patent: Aug. 17, 1993

[54] APPARATUS AND METHOD FOR NON-DESTRUCTIVE TESTING USING MULTI-FREQUENCY EDDY CURRENTS

[75] Inventor: Kristina H. V. Hedengren, Schenectady, N.Y.

[73] Assignee: General Electric Company, Schenectady, N.Y.

[21] Appl. No.: 696,457

[22] Filed: May 6, 1991

[51] Int. Cl.$^5$ ............................................. G01N 27/90
[52] U.S. Cl. ................................... 324/232; 324/238; 324/240
[58] Field of Search ............... 324/232, 233, 234, 236, 324/237, 238, 239, 240, 241, 242, 243, 227

[56] References Cited

U.S. PATENT DOCUMENTS

| | | | |
|---|---|---|---|
| 4,467,281 | 8/1984 | Davis et al. | 324/232 |
| 4,563,644 | 1/1986 | Lenander et al. | 324/232 |
| 4,652,822 | 3/1987 | Wallace | 324/232 |
| 4,757,259 | 7/1988 | Charpentier | 324/232 X |
| 4,816,758 | 3/1989 | Theissen et al. | 324/232 X |
| 4,855,677 | 8/1989 | Clark, Jr. et al. | 324/232 X |
| 4,965,519 | 10/1990 | Tornblom | 324/225 |
| 5,047,719 | 9/1991 | Johnson et al. | 324/242 |

OTHER PUBLICATIONS

"Eddy Current Imaging for Defect Characterization," David C. Copley, GE/Aircraft Engine Business Group, Evendale, Ohio, Review of Progress in Quantitative Nondestructive Evaluation, vol. 2B, Plenum Press, New York, 1983, pp. 1527-1540.

"Use of Imaging Techniques for Eddy Current NDE," K. H. Hedengren, R. O. McCary and J. D. Young, GE/CR&D, Schenectady, N.Y., Review of Progress in Quantitative Nondestructive Evaluation, vol. 7A, Edited by Donald O. Thompson and Dale E. Chimenti (Plenum Publishing Corp., 1988), pp. 357-365.

"Flexible Substrate Eddy Current Coil Arrays," Y. D. Krampfner, D. D. Johnson, Review of Progress in Quantitative Nondestructive Evaluation, vol. 7A, pp. 471-478, 1988.

"Eddy Current Image Processing for Crack Size Characterization," R. O. McCary, GE Co., Corporate Research and Development, Review of Progress in Quantitative Nondestructive Evaluation, vol. 8A, Edited by D. O. Thompson and D. E. Chimenti, Plenum Press, New York, 1990, pp. 773-780.

"An Analysis of Multifrequency Eddy Current Mixing Parameters in Tubing Inspection," Louis de la Pintiere, Intercontrole.

"Eddy Current Printed Circuit Probe Array: Phase I," T. G. Kincaid Signametrics Report No. 9, Sep. 12, 1987, (also appeared as an appendix to a GE Final Report).

*Primary Examiner*—Gerard R. Strecker
*Assistant Examiner*—Warren S. Edmonds
*Attorney, Agent, or Firm*—James R. McDaniel; Paul R. Webb, II

[57] ABSTRACT

A method for improving eddy current flaw detection by simultaneously exciting a select plurality of eddy current probe elements with a multiplicity of select frequencies in a simultaneous parallel or serial manner to form a corresponding multiplicity of direct and/or differential images which can be processed together for improved eddy current image resolution. Select eddy current probe elements when driven at select multiple frequencies further provide a capability for simultaneous flaw detection and characterization by dual resolution scanning. Dual flaw resolution is accomplished by first locating a flaw using low resolution frequencies; and thereupon, switching to higher resolution frequencies to characterize the flaw.

17 Claims, 5 Drawing Sheets

APPARATUS AND METHOD FOR NON-DESTRUCTIVE TESTING USING MULTI-FREQUENCY EDDY CURRENTS

RELATED APPLICATIONS

The present application is related to patent application Ser. No. 07/696,456, now U.S. Pat. No. 5,182,513, entitled "Method and Apparatus for Nondestructive Surface Flaw Detection" by John D. Young et al, which discloses and claims a method and apparatus for multi-frequency driving to obtain a plurality of synchronized, spatially correlated, discrete eddy current measurement signals and multi-channel acquisition thereof for image processing. This eddy current inspection system is herein considered the preferred embodiment of the present application. Application Ser. No. 07/696,455 entitled "Eddy Current Probe Arrays" by Kristina H. Hedengren et al discloses and claims a multi-layer, integrated probe array comprised of a plurality of sufficiently distributed, precisely fabricated probe elements disposed in a flexibly conforming, multi-layer structure in order to accommodate inspection of geometrically difficult surfaces in a single scan. Both referenced applications are assigned to the same assignee as the present application and are filed concurrently herewith being incorporated herein by reference in their entireties.

Co-pending application Ser. No. 07/504,769, now abandoned, entitled "A Flexible Interconnected System" by Charles W. Eichelberger, et al describes a multi-layer, multi-component integrated fabrication technology suitable for making flexible, spatially correlated, probe arrays for inspecting difficult surface geometries. This co-pending application is assigned to the same assignee as the present application and is incorporated herein by reference in its entirety.

FIELD OF INVENTION

This invention generally relates to multi-frequency eddy current non-destructive testing and more particularly to driving a plurality of eddy current probe elements with a multi-frequency excitation to simultaneously improve flaw detection sensitivity and image resolution by providing speed, accuracy and reliability.

BACKGROUND OF THE INVENTION

Nondestructive eddy current technology is an established technology and various inspection techniques exist. Various types of eddy current probes and probe arrays exist. A probe array for an inspection system is typically comprised of a plurality of like probe elements. Most often the elements are traditional eddy current probes which are used in conventional mechanical scanning modes. Scanning is accomplished using typical probes operating in a bridge circuit or in reflection mode. Such probes utilize multi-turn induction coils often surrounding ferrite cores to intensify induced magnetic field flux. In reflection mode, one of the induction coils, the drive coil, is disposed very near the surface of a conductive part undergoing inspection and driven by an alternating current source to create a flux of magnetic field into and below the conductive surface. This flux causes local current to flow in the conductive part. This local current flow creates magnetic flux of its own. A complementary coil, the sense coil, operates to receive current mutually induced by the resultant flux due to current flow through the conductive part. Any flaw or defect in the near surface integrity of the conductive part will disrupt the flow of induced current. This disruption is detected as a change in voltage as detected by the sense coil.

A standard eddy current probe generally has coils disposed within close proximity of one another in order to responsively detect voltage changes induced by surface current disruptions. The probes may differ in their winding arrangement and coil connections. Coils may be wound in the same or opposite directions. The output is a differential voltage which may be used to produce an eddy current image. Response signals are collected from such probes by using manual or mechanical scanning modes. Scanning along the surface of the conductive part being inspected is typically accomplished by moving a single probe across the conductive surface to cover all regions of interest. This simple scanning measurement approach detects flaws by thresholding, i.e. using a pre-selected threshold to determine if a flaw signal is present. A primary problem with thresholding involves distinguishing a small disruptive flaw signal above background noise. The detection problem is complicated further as eddy current probes are themselves a source of great variability. In addition, the overwhelming relative size difference between the probe size and the flaw size causes spatial blurring in the resultant image.

Electromagnetic sensor arrays are a well established art; however, little has been done to apply the techniques employed for electromagnetic sensor array signal collection and image processing to eddy current nondestructive testing. It is recognized that scan rate efficiency is increased if probes are configured into surface measurement arrays so that large planar inspection surfaces can be scanned. Planar probe arrays typically employ like eddy current probes. Probe sensitivity to flaw detection is limited by the relative size of the probe sense element. It has been suggested that printed circuit technology be applied to fabricate more sensitive arrays by decreasing sense coil size. However, conventional printed circuit technology cannot achieve the miniaturization required to achieve current U.S. Government standards for flaw detection in difficult geometries like aircraft engines. Although it has been suggested that multi-layer printed circuit probe arrays could be implemented, there has been no suggestion that these arrays be driven using multi-frequency excitation, whether simultaneously mixed or independently applied.

Multi-frequency inspection techniques are not new. Multi-frequency techniques have been conventionally applied to achieve suppression of unwanted signals often due to the geometry of the surface under inspection. Simultaneous parallel frequency mixing or serial frequency mixing is conventionally applied to "blank" one or more unwanted signals. The multi-frequency driving technique has not been applied to an eddy current array probe, nor has frequency mixing of this sort been used to simultaneously "tune" flux penetration depth governing eddy current detection and flaw resolution sensitivity. Furthermore, the technique is not typically applied to a multiplicity of different probe elements. The operating frequency sensitivities of many different probe elements can be selected to provide specific depth penetration then drives can be switched among the probe elements to provide high and low resolution scanning. This provides a "selective" tuning capability. This novel capability relies on operational features of the eddy current inspection system described in patent application Ser. No. 07/699,456, entitled "Method and Apparatus for Nondestructive Surface Flaw Detection" by John D. Young et al. The notion of driving select multiple probe elements having unique characteristics with select multiple drive frequencies in order to tailor detection sensitivity is new.

OBJECTS OF THE INVENTION

An object of this invention is to provide a method for driving an eddy current probe array having a plurality of eddy current probe elements with a multiplicity of excitation frequencies in order to simultaneously improve flaw detection and image resolution.

Another object of this invention is to provide a method for improving image or signal resolution by processing multiple images or signals resulting from independent, sequential or simultaneous excitation using a multiplicity of excitation frequencies.

Yet another object of this invention is to selectively combine a multiplicity of excitation frequencies with a corresponding selection of unique eddy current probe elements to provide a flaw detection sensitivity feature which can accommodate changes in resolution sensitivity during scanning.

A further object of the invention is to improve image resolution by utilizing direct images in cooperation with differential images formed by driving a multiplicity of eddy current probe elements with a corresponding multiplicity of frequencies.

A still further object of the invention is to apply the above to an eddy current array probe.

A final object of the invention is to speed up the inspection process while improving accuracy, resolution and reliability.

SUMMARY OF THE INVENTION

The present invention is generally directed to improving eddy current sensing and more particularly directed to exciting a multiplicity of eddy current probe elements with a multiplicity of frequencies in a simultaneous, parallel or serial manner to form multiple simultaneous and differential images which can be processed together to improve image resolution. Select eddy current probe elements when driven at select multiple frequencies provide a capability for adjusting the range of probe depth penetration and thereby flaw detection resolution sensitivity to better resolve a flaw without additional scanning requirements.

A plurality of like probe elements simultaneously driven by a multiplicity of unlike frequencies provide a corresponding multiplicity of unlike images to improve resolution without requiring additional scan time. A plurality of like probe elements driven in parallel by a multiplicity of like frequencies provides a correspondingly faster image. A plurality of probe elements having predetermined characteristics being selectively driven by a multiplicity of predetermined frequencies can accommodate selective flaw detection resolution and/or characterization with minimal scanning time requirements. Selective sensitivity ranging of an array probe can be accomplished using specific probe elements in combination with select drive frequencies. An array comprising a plurality of spatially correlated probe elements whose outputs are differentially interconnected operates as a differential probe array even when said elements are not differential probes.

DESCRIPTION OF THE DRAWINGS

While the novel features of the invention are set forth with particularity in the appended claims the invention, both as to organization and content, will be better understood and appreciated, along with other objects and features thereof, from the following detailed description taken in conjunction with the drawings in which:

DETAILED DESCRIPTION OF THE INVENTION

Figure 1A:
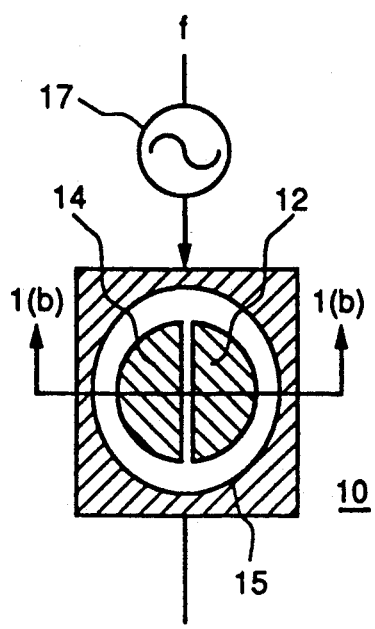
FIG. 1(a) is a facing view of a typical split core differential (SCD) eddy current probe element.
Figure 1B:
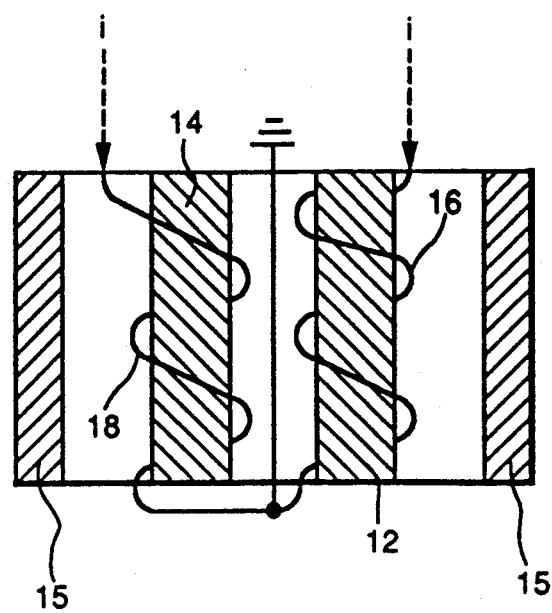
FIG. 1(b) is a cross sectional side view identified in FIG. 1(a) through the SCD eddy current probe element.
Figure 1C:
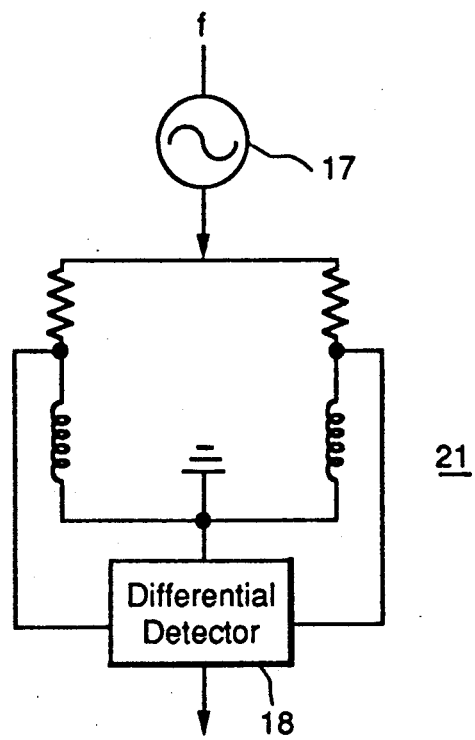
FIG. 1(c) is a circuit diagram of a bridge circuit for characterizing detection in differential mode using the typical SCD eddy current probe of FIGS. 1(a) and 1(b)

In FIG. 1(a) a conventional split core differential (SCD) probe element 10 is shown to be used for the operational description of the invention although other types of probes, such as absolute probes, and other operating modes, such as reflection mode, are within the scope of the invention. FIG. 1(a) shows a face and side view of a typical split core differential probe wherein the shaded regions identify ferrite. In FIG. 1(b) coils 16 and 18 are wound in the same direction around two ferrite cores 12 and 14 respectively and enclosed by a ferrite casing 15. The windings are differentially connected as shown in FIG. 1(c) and driven by an oscillating current source 17 typically at a single frequency as indicated by an "f". Detection is accomplished utilizing the underlying bridge circuit 21 which is herein shown to electrically characterize the split core differential probe via inductor coils 16 and 18. The flaw signal detected 18 is characterized by a differential output voltage across the bridge, i.e. between the coils.

Figure 2:
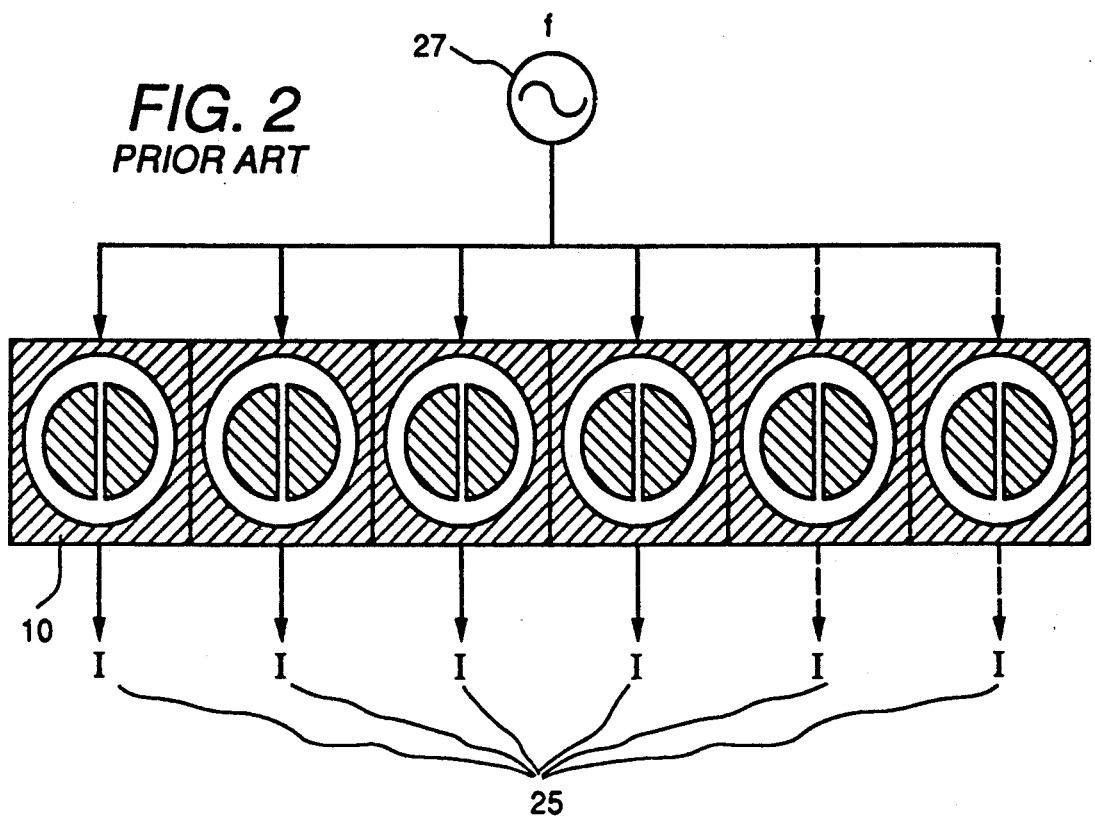
FIG. 2 is a schematic diagram of a single frequency oscillating current source driving a plurality of like SCD eddy current probe elements.

FIG. 2 shows a plurality of such SCD probe elements collectively excited by a single frequency drive 27 to produce a corresponding multiplicity of related images 25. The plurality of probe elements operates as a simultaneously excited probe array to provide faster image formation. This is due to spatially correlated, repetitive scanning which at the same frequency decreases the time needed to produce an image by increasing scanning coverage.

Figure 3:
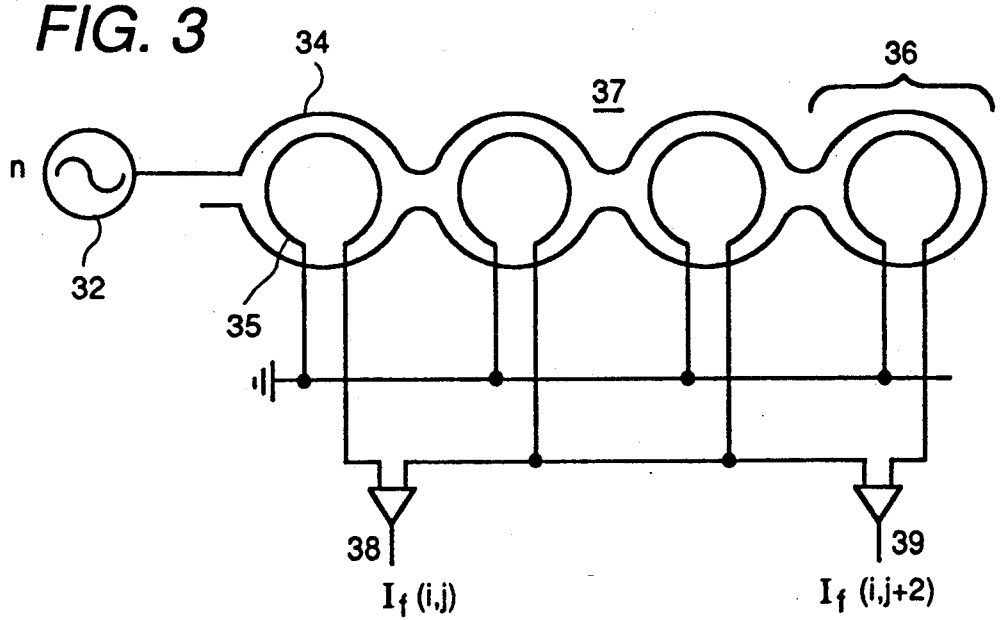
FIG. 3 is a prior art schematic diagram of an array of like probe elements; wherein alternate pairs of elements operating in reflection mode are differentially interconnected and driven by a single frequency.

FIG. 3 shows a prior art eddy current printed circuit probe array 37 wherein probe elements 36 are operating in reflection mode. Probe elements are interconnected wherein each consists of a drive coil 34 driven by a single frequency oscillating current source 32 and a corresponding sense coil 35. The output from alternate probe element pairs are differentially connected to form a multiplicity of images 38 39 corresponding to each alternate probe element pair of the array. By so connecting, distinct, alternate probe pairs are treated as array elements.

In FIGS. 4-9, there are shown improved methods of resolving an eddy current image in accordance with the present invention.

Figure 4:
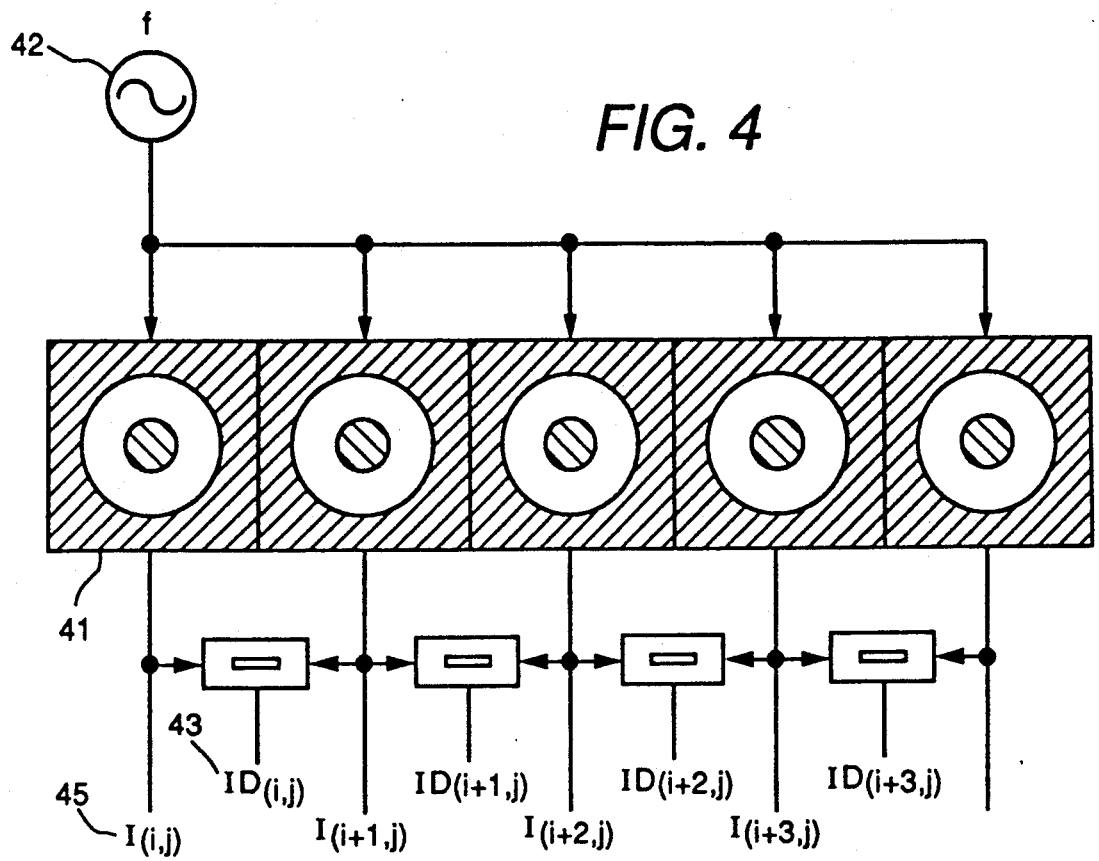
FIG. 4 is a schematic diagram of a plurality of like probe elements wherein each sequential pair of elements is differentially interconnected and driven by a single frequency.

In FIG. 4 a plurality of like probes 41, not necessarily comprising a probe array, are collectively driven by a single frequency 42 wherein the difference image formed between each probe element pair 43 as well as the image corresponding to each probe element 45 are available for image processing in order to improve signal detection over noise thereby improving detection and characterization of flaw images. The plurality of probe element pairs are differentially interconnected at their outputs; allowing an extra differential image (one more than was available in prior art FIG. 3) to be implemented in image processing to improve resolution even further. This differentially developed improvement to image resolution treats each probe pair as an array element. The concept can be applied to other types of probe elements as well.

Figure 5:
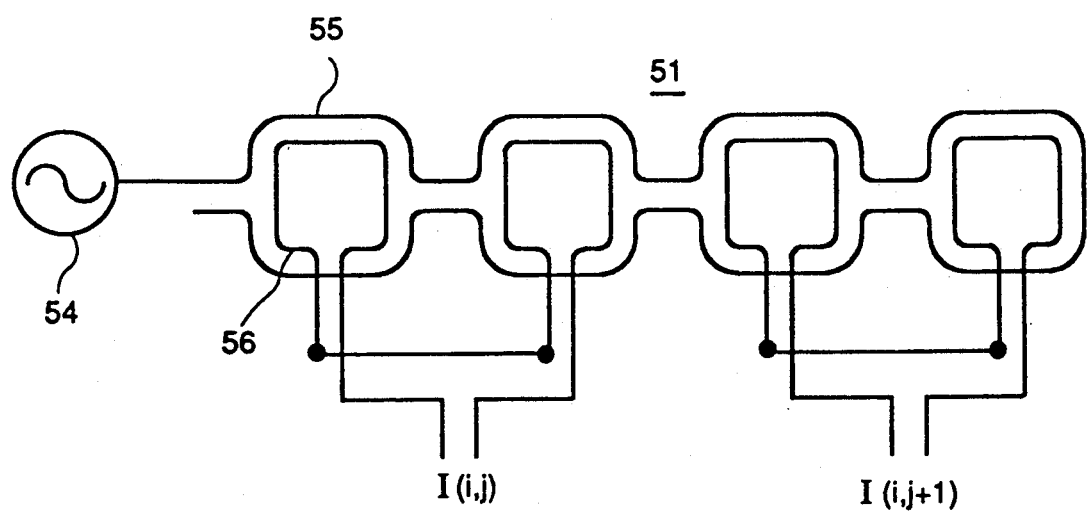
FIG. 5 is a schematic of a flexible, multi-layer probe array fabricated in accordance with application Ser. No. 07/696,455, entitled "Eddy Current Probe Arrays" by Kristina H. et al differentially interconnected and by a single frequency.

FIG. 5 applies the differential output interconnection of FIG. 4 to probe array 51 comprised of like probe elements 53 operating in reflection mode. Note the probe array utilized herein is fabricated according to application Ser. No. 07/696,455, entitled "Eddy Current Probe Arrays" by Kristina H. Hedengren et al rather than utilizing the prior art printed circuit probe array of FIG. 3. Array 51 is serially driven at a single frequency 54 through drive coil 55 wherein probe drive coil elements have been interconnected. Probe array sense coil outputs are differentially interconnected in pairwise fashion to produce a "virtual ground" as opposed to the use of a physical ground as in prior art FIG. 3. Resolution depends on the size and spacing between the sense coils. The multi-channel, multi-frequency eddy current inspection system described in patent application Ser. No. 07/696,456, entitled "Method and Apparatus for Nondestructive Surface Flaw Detection" by John D. Young et al, accommodates single frequency driving of eddy current probe array 51 with sensing in a parallel manner. Array 51 can accommodate inspection of large surfaces. A flexible eddy current surface measurement array can accommodate inspection of geometrically difficult geometries as well. The use of a probe array eliminates registration problems associated with probe alignment for proper scanning.

Figure 6:
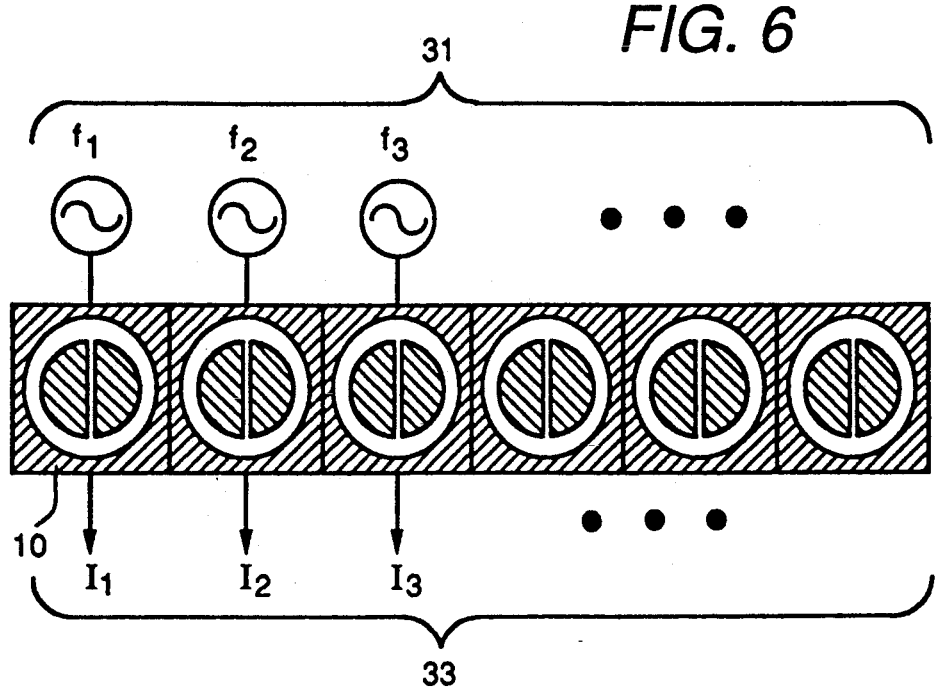
FIG. 6 is a schematic diagram of a plurality of like SCD eddy current probe elements, each individually driven by a different frequency in accordance with the present invention.

In FIG. 6 a plurality of like SCD probe elements 10 are driven separately using a simultaneously applied multiplicity of unlike frequencies 31 to individually drive elements of the plurality to produce a corresponding multiplicity of different images 33 at the same scan rate required to produce a single image. All images can be perfectly registered by proper spatial shifting of the image data. Since flux penetration is directly related to drive frequency, images are formed corresponding to various penetration depths. Thus, a new feature for selecting depth penetration in eddy current flaw detection is provided by multi-frequency driving of arrays. Furthermore, the redundant image data can be used to remove background nonuniformities by proper selection of driving frequencies.

Figure 7:
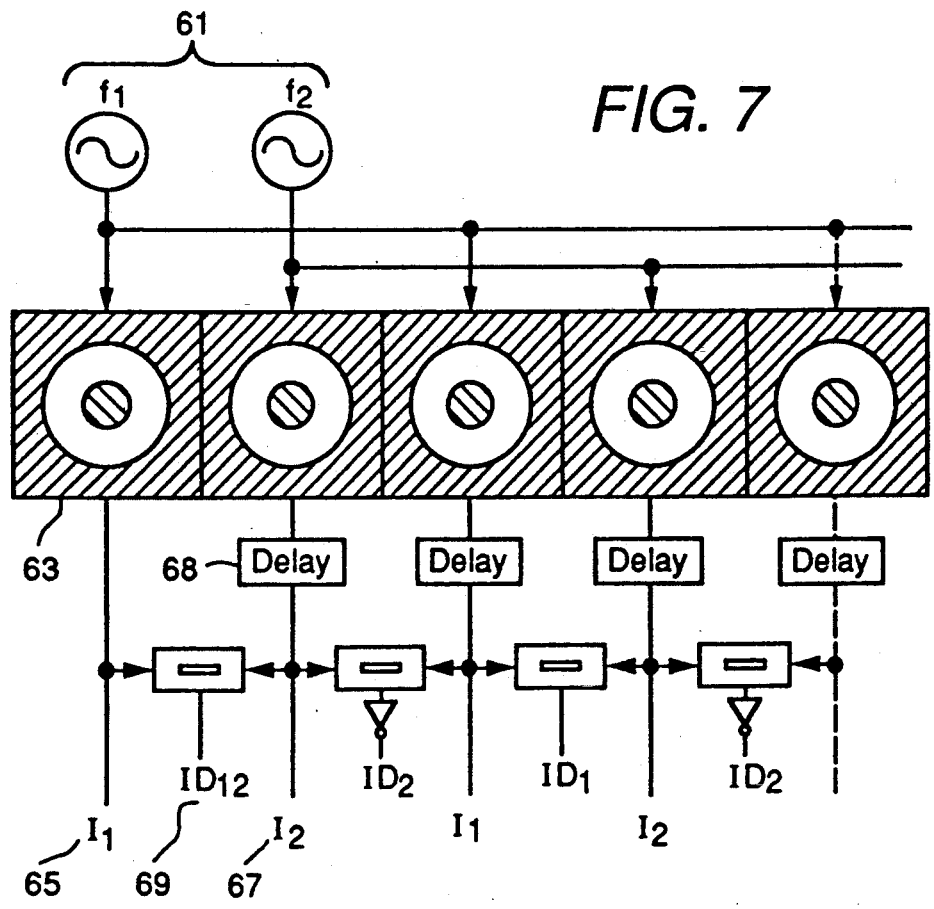
FIG. 7 is a schematic like that of FIG. 4(a) wherein the plurality of like probe elements is driven by a multiplicity of frequencies.

FIG. 7 shows a dual frequency serially driven 61 plurality of like eddy current probe elements 63. Two images, 65 and 67, corresponding to dual frequencies identified at 61 are produced in addition to an associated frequency difference image 69. Appropriate delays, as indicated at 68, are introduced so that the frequency difference image is spatially registered for image processing. Although illustrated for a dual frequency drive; a multiplicity of driving frequencies is understood to be within the scope of the invention.

Figure 8:
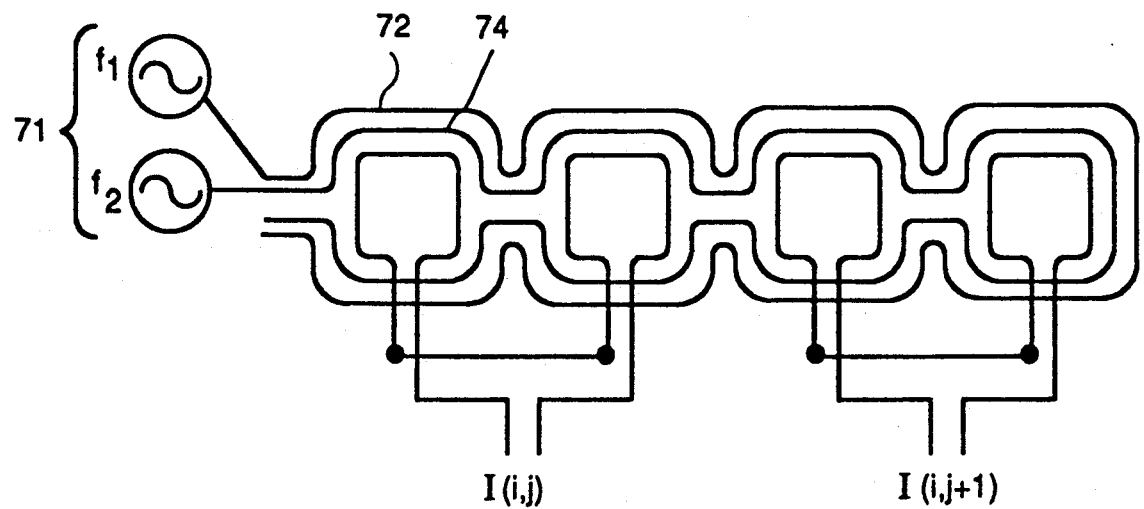
FIG. 8 is a schematic like that of FIG. 4 wherein a probe array of like probe elements is collectively driven by a multiplicity of frequencies.

FIG. 8 shows multi-frequency driving of the eddy current probe array described in FIG. 5 wherein drive coils, 72 and 74, simultaneously excite a plurality of sense coils with corresponding frequencies, f1 and f2, indicated at 71. The coils can be laid out in a planar configuration or, using multi-layer fabrication, in parallel coplanar layers, wherein this overlapped configuration permits the coils to sense the same portion of the inspection surface. In this way multi-layer drives can be simultaneously applied.

Figure 9:
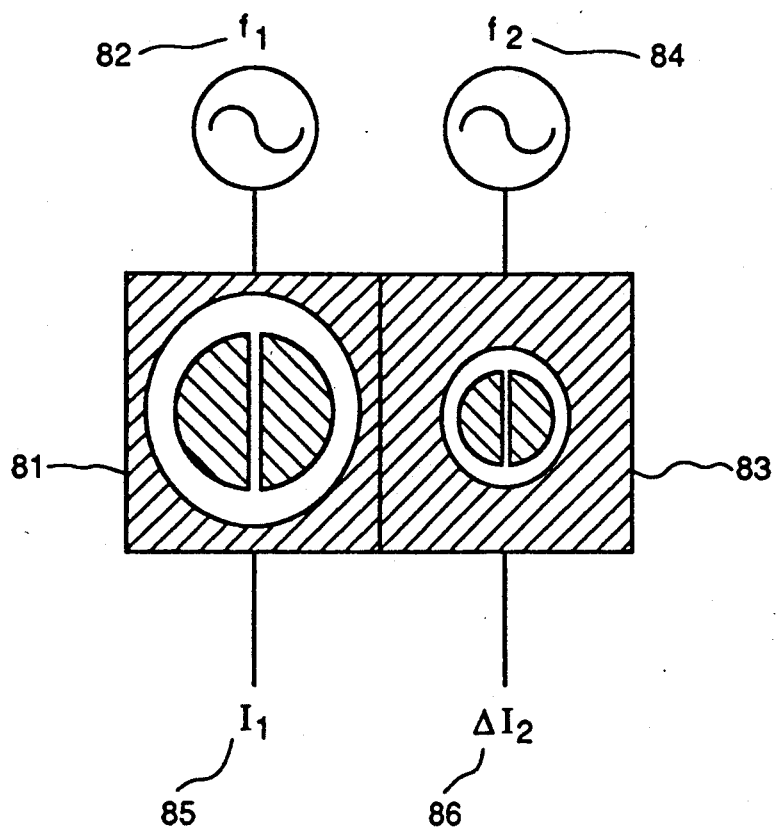
FIG. 9 is a schematic diagram of a plurality of two unlike SCD probe elements individually driven by select unlike frequencies.

FIG. 9 illustrates array differences wherein distinctly different probe elements 81 and 83 are driven individually by distinctly different drive frequencies 82 and 84 to form distinctly different corresponding images 85 and 86. The combination of probe element size and type with selective frequency driving provides a mechanism for simultaneous multi-resolution imaging. The multiple, unlike, probe elements of varying sensitivity characteristic 81, 83 operate as frequency selective 'coarse' and 'fine' adjustments to 'tune' flaw detection. For example, a large probe 81 can locate a flaw with minimum sensitivity using coarse spacing and fast inspection rates. Thereupon, a smaller probe element 83 having more resolution due to its decreased size, can then characterize the flaw with greater sensitivity given the accurate flaw registration predetermined by the previous large probe element scan. In this way, low resolution, fast scanning is cooperatively combined with high resolution scanning to quickly locate a flaw with low resolution using coarse spacing and fast inspection rates. Thereupon, a smaller probe element 83 having finer resolution due to its decreased size, can then characterize the flaw with greater sensitivity given the accurate flaw registration predetermined by the previous large probe element scan. In this way, fast scanning can detect a flaw; then by switching frequency drives other probe elements operating at higher resolution repeat or continue scanning at finer resolution to characterize the flaw. Similarly a low frequency scan combined with a high frequency scan provides a mechanism for removing unwanted signals.

In the operation of the method of the present invention an eddy current image is improved by providing selective multi-frequency drives which are applied as independent, simultaneous or sequential excitation to a plurality of eddy current probe elements to produce a corresponding multiplicity of frequency images for concurrent image processing.

The notion of driving multiple probe elements either separately using independent multiple frequencies, or simultaneously using parallel or serial multiple frequency drives provides an improved imaging capability heretofore unavailable. A multi-frequency driving means for accomplishing multi-frequency eddy current sensing is provided by a multi-channel, multi-frequency eddy current inspection system described in patent application Ser. No. 07/696,456, entitled "Method and Apparatus for Nondestructive Surface Flaw Detection" by John D. Young et al. The notion of utilizing eddy current sense elements with unique characteristics in cooperation with multi-frequency drive excitation to coarsely sense the flaw then refine sensing resolution to characterize the flaw through the implementation of a plurality of probes or a probe array is a novel method for improving eddy current inspection in an industrial environment.

While a specific embodiment of the invention has been illustrated and described herein, it is realized that numerous modifications and changes will occur to those skilled in the art. It is therefore to be understood that the appended claims are intended to cover all such modifications and changes as fall within the true spirit and scope of the invention.

I claim:

1. A method of improving eddy current flaw detection and resolution comprising the steps of:
   providing a plurality of probe elements;
   providing an alternating source of current capable of oscillating at a multiplicity of discrete frequencies;
   simultaneously driving said plurality of probe elements with said multiplicity of frequencies to excite discrete frequency responsive signals therefrom;
   scanning to acquire a corresponding multiplicity of discrete frequency responsive signals from each probe element of said plurality of probe elements; and
   resolving a corresponding multiplicity of eddy current images from said scan responsive multiplicity of frequency responsive signals.

2. Method according to claim 1 wherein said step of driving further includes applying at least one frequency to each select probe element.

3. Method according to claim 1 wherein said step of driving further includes selectively applying said frequencies to said select plurality of probes in a parallel manner.

4. Method according to claim 1 wherein said step of driving further includes selectively applying said frequencies to said select plurality of probes in a serial manner.

5. Method according to claim 1 wherein said probe elements are substantially similar.

6. Method according to claim 1 wherein frequencies of said multiplicity are selectively dissimilar providing correspondingly dissimilar frequency responsive signals.

7. Method according to claim 1 wherein said scanning step is accomplished in a time period no greater than that required for single frequency excitation.

8. Method according to claim 5 wherein frequencies of said multiplicity are selectively similar providing correspondingly similar frequency responsive signals.

9. Method according to claim 8 wherein said scanning step is accomplished in a time period less than that required for single frequency excitation.

10. Method according to claim 1 wherein said probe elements are dissimilar.

11. Method according to claim 10 wherein said select probe elements have characteristics predetermined to correspond to desired flaw detection and characterization limits.

12. Method according to claim 11 wherein said multiplicity of frequencies is selectively predetermined to provide a selective flaw detection sensitivity feature responsive to said characteristics.

13. Method according to claim 12 wherein selective flaw detection is accomplished in a single scan.

14. A method according to claim 13 wherein said selective flaw detection sensitivity feature further comprises selectively switching from low resolution scanning after detecting a flaw to high resolution scanning in order to characterize said flaw.

15. A method according to claim 13 wherein said selective flaw detection sensitivity feature further comprises selectively switching from high resolution scanning upon characterizing a flaw to low resolution scanning in order to detect additional flaws.

16. Method according to claim 1 wherein said plurality of probe elements are spatially correlated to provide an eddy current probe array.

17. Method according to claim 1 further including differencing select pairs of said signals in order to resolve difference images therefrom.

* * * * *